US006780159B2

(12) United States Patent
Sandler et al.

(10) Patent No.: US 6,780,159 B2
(45) Date of Patent: Aug. 24, 2004

(54) ACOUSTIC DETECTION OF VASCULAR CONDITIONS

(75) Inventors: Richard H. Sandler, Evanston, IL (US); Hussein A. Mansy, Justice, IL (US)

(73) Assignee: Biomedical Acoustic Research Corporation, Evanston, IL (US)

( * ) Notice: Subject to any disclaimer, the term of this patent is extended or adjusted under 35 U.S.C. 154(b) by 193 days.

(21) Appl. No.: 10/046,863

(22) Filed: Jan. 15, 2002

(65) Prior Publication Data

US 2002/0099286 A1 Jul. 25, 2002

Related U.S. Application Data

(60) Provisional application No. 60/261,997, filed on Jan. 16, 2001.

(51) Int. Cl.[7] .................................................. A61B 5/00
(52) U.S. Cl. ........................ 600/504; 600/505; 600/586; 600/528; 600/587
(58) Field of Search ............................. 600/505, 586, 600/587, 528, 504

(56) References Cited

U.S. PATENT DOCUMENTS

| | | | | | |
|---|---|---|---|---|---|
| 3,563,232 | A | * | 2/1971 | Webb et al. | 600/528 |
| 5,012,815 | A | * | 5/1991 | Bennett et al. | 600/528 |
| 5,109,863 | A | * | 5/1992 | Semmlow et al. | 600/528 |
| 5,727,561 | A | * | 3/1998 | Owsley | 600/504 |
| 6,048,319 | A | * | 4/2000 | Hudgins et al. | 600/528 |

OTHER PUBLICATIONS

Abdallah SA et al.; "Arterial Stenosis Murmurs: An Analysis of Flow and Pressure Fields;" J Acoust Soc Am 83:318–34; 1988.

Akay YM et al; "Dynamics of the Sounds Caused by Partially Occluded Femoral Arteries in Dogs;" Ann of Biomed Eng 22:493–500; 1994.
Anonymous. "NKF–DOQI Clinical Practice Guidelines for Vascular Access;" National Kidney Foundation–Dialysis Outcomes Quality Initiative; Am J Kidney Dis 30:S150–91; 1997.
Ask P et al; "Bio–acoustic Signals from Stenotic Tube Flow: State of the Art and Perspectives for Future Methodological Development;" Med Biol Eng Comp 33:669–75; 1995.
Back L et al; "Shear–layer Flow Regimes and Wave Instabilities and Reattachment Lengths Downstream of an Abrupt Circular Channel Expansion;" ASME J Appl Mech 39:677–81; 1972.
Beathard GA; Physical Examination of AV Grafts; Sem Dial 5:74; 1996.
Beathard GA et al; "Percutaneous Angioplasty for the Treatment of Venous Stenosis: A Nephrologists View;" Sem Dial 8:166–170; 1995.
Besarab A et al; "Utility of Intra–access Pressure Monitoring In Detecting and Correcting Venous Outlet Stenoses Prior to Thrombosis;" Kidney Int 47:1364–1373; 1995.
Burger H et al.; "Percutaneous Transluminal Angioplasty Improves Longevity in Fistulae and Shunts for Hemodialysis;" Nephrol Dial Transplant 5:608–611; 1990

(List continued on next page.)

*Primary Examiner*—Robert L. Nasser
(74) *Attorney, Agent, or Firm*—Grossman & Flight, LLC

(57) ABSTRACT

A system and method of detecting a vascular condition within a body receives vibrations emitted in response to blood flowing through a vascular structure within the body and converts the received vibrations into vibration information. The system and method generates spectral information from the vibration information, calculates a spectral parameter based on the spectral information and detects the vascular condition based on the spectral parameter.

39 Claims, 7 Drawing Sheets

OTHER PUBLICATIONS

Etheredge EE et al; "Salvage Operations for Malfunctioning Polytetrafluoroethylene Hemodialysis Access Grafts;" Surgery 94:464–470; 1983.

Fillinger MF et al. "Graft Geometry and Venous Intimal–medial hyperplasia in Arteriovenous Loop Grafts;" J of Vas Surg 11:556–66; 1990.

Fillinger MF et al; "Does the End–to–end Venous Anastomosis Offer a Functional Advantage Over the End–to–side Venous Anastomosis in High–output Arteriovenous grafts?" J Vas Surg 12:676–690; 1990.

Fillinger MF et al; "Hemodynamics and Intimal Hyperplasia, Chapter 2 of Vascular Access for Hemodialysis–II;" "W.L. Gore & Associates, Inc., and Precept Press, Inc. (B.G. Sommer and M.L. Henry, Eds.)" 21–51; 1991.

Fox B et al; "Distribution of Fatty and Fibrous Plaques in Young Human Coronary Arteries;" Atherosclerosis 41:337–347;1982.

Gallego Beuter JJ et al; "Early Detection and Treatment of Hemodialysis Access Dysfuction;" Cardiovasc Intervent Radiol 23:40–6; 2000.

Glagov S; "Intimal Hyperplasia, Vascular Modeling, and the Restenosis Problem;" Circulation 89(6):2888–91; 1994.

Hodges TC et al; "Longitudinal Comparison of Dialysis Access Methods: Risk Factors for Failure;" J Vasc Surg 26:1009–19; 1997.

Kanterman RY et al; "Dialysis Access Grafts: Anatomic location of Venous Stensis and Results of Angioplasty;" Radiology 195–135–9; 1995.

Kartchner MM et al; Non–invasive Detection and Evaluation of Carotid Occlusive Disease Arch Surg 106:528–35; 1973.

Katz SG et al; "The Percutaneous Treatment of Angioaccess Graft Complications;" Am J Surg 170:238–42; 1995.

Kirkeeide RL et al; "Wall Vibrations Induced by Flow Through Simulated Stenosis in Models and Arteries;" J Biomech 10:431–41; 1977.

Kong X et al; "Multi–resolution Analysis of Gastrointestinal Sounds for Small Bowel Obstruction Identification;" Int J Comp App 8(1):7–12; 2001.

Ku DN et al; "Flow Patterns in the Abdominal Aorta Under Simulated Postprandial and Exercise Conditions: An Experimental Study;" J Vasc Surg 9:309–316; 1989.

Mansy HA et al; "Symmetry of Interacting Modes in a Cylinder Wake;" J Phy Fluids 3:2047–2049; 1991.

Mansy HA et al; "Bowel–sound Signal Enhancement Using Adaptive Filtering;" IEEE Eng Med Diol 16:105–17; 1997.

Mansy HA et al; "Choice of Operating Parameters in Heart Sound Removal from Bowel Sounds Using Adaptive Filtering;" IEEE/EMBS Annual Conference Proceedings 19:106–109; 1997.

Mansy HA et al; "A New Acoustic Method for Immediate Pneumoperitoneum Detection;" J Pediatr Gastroenterol Nutr 27:486; 1998.

Mansy HA et al; "Detection an Analysis of Gastrointestinal Sounds in Normal and Small Bowel Obstructed Rats;" Med Biol Eng Comput 38:42–48; 2000.

Martin LG et al; "Prophylactic Angioplasty Reduces Thrombosis in Virgin ePTFE Arteriovenous Dialysis Grafts with Greater Than 50% Stenosis: Subject Analysis of a Prospectively Randomized Study;" J Vasc Interv Radiol 10:389–96; 1999.

Masawa N et al; "Quantitative Morphologic Study of Intimal Thickening at the Human Carotid Bifurcation. I. Axial and Circumferential Distribution of Maximum Intimal Thickening in Asymptomatic Uncomplicated Plaques;" Atherosclerosis 107:137–146; 1994.

Moore JE et al; "Fluid Wall Shear Stress Measurements in a Model of the Human Abdominal Aorta: Oscillatory Behavior and Relationship to Artheroschlerosis;" Atherosclerosis 110:225–240;1994.

Padmanabhan V et al; "Accelerometer Type Cardiac Transducer for Detection of Low–level Heart Sounds;" IEEE Trans Biomed Eng 40:21–8; 1993.

Palder SB et al; "Vascular Access for Hemodialysis: Patency Rates and Results of Revision;" Ann Surg 202:235–239; 1985.

Pasterkamp H et al; "Measurement of Respiratory Acoustical Signals: Comparison of Sensors;" Chest 104:1518–25; 1995.

Sandler RH et al; "Computerized Analysis of Bowel Sounds in Normal and Small Bowel Obstructed Rats;" J Pediatr Gastroenterol Nutr 23:369d; 1996.

Sandler RH et al; "Computerized Analysis of Bowel Sounds in Normal Fed and Fasted Human Subjects;" Gastroenterology 110:A752; 1996.

Sandler RH et al; "Computerized Analysis of Bowel Sounds in Human Subjects with Mechanical Bowel Obstruction vs Ileus;" AGA Abstract A752.

Sandler RH et al; "Computerized Analysis of Swallowing Sounds (CASS) in Normal Subjects;" Am J Gastroentr 92:1602; 1997.

Svindland A; "The Localization of Sudanophilic and Fibrous Plaques in the Main Left Coronary Bifurcation;" Atherosclerosis 48:139–145; 1983.

Trerotola SO et al; "Screening for Dialysis Access Graft Malfunction: Comparison of Physical Examination with US;" J Vas Interv Radiol 7:15–20; 1996.

Verburg J et al; "Phonography: Physical and Technical Aspects and Clinical Uses;" Non–invasive physiological measurements—ed. P. Rolfe; Academic Press, New York 1979.

Vermarin H et al; "The Recording of Heart Vibrations: A Problem of Vibration Measurement on Soft Tissue;" Med Biol Eng Comput 22: 168–78; 1984.

Wang JA et al; "Modeling Sound Generation in Stenosed Coronary Arteries;" IEEE Trans Biomed Eng 37:1087–94; 1990.

Williams DR et al; "The response and symmetry properties of a cylinder Wake Subject to Localized Surface Excitation;" J Fluid Mechanics 234:71–96; 1992.

Windus DW et al; "Optimization of High–efficiency Hemodialysis by Detection and Correction of Fistula Dysfunction;" Kidney Int 38:337–341;1990.

Wodlicka GR et al; "Phase Delay of Pulmonary Acoustic Transmission from Trachea to Chest Wall;" IEEE Trans Biomed Eng 39:1053–8; 1992.

Zarins CK et al; "Carotid Bifurcation Atherosclerosis: Quantitive Correlation of Plaque Localization with Flow Velocity Profiles and Wall Shear Stress;" Circ Res 53:502–514; 1983.

* cited by examiner

ACOUSTIC DETECTION OF VASCULAR CONDITIONS

RELATED APPLICATION

This application claims the benefit of the filing date of U.S. provisional patent application No. 60/261,997, entitled "Acoustic Detection of Vascular Conditions," filed on Jan. 16, 2001.

BACKGROUND OF THE INVENTION

1. Technical Field

The present invention relates generally to the non-invasive diagnosis of conditions within a human or animal body and, more particularly, the invention relates to diagnostic apparatus and techniques that use the acoustic characteristics of vascular blood flow to assess vascular conditions.

2. Description of Related Technology

Assessment of vascular (i.e., artery and vein) conditions is crucial to the diagnosis of many serious, and often life threatening, pathologies. For example, vascular occlusions, which commonly take the form of atherosclerotic vessel disease, can reduce or eliminate the flow of blood to critical organs within a body, thereby causing illness, disability and death. In particular, one or both of the carotid arteries supplying blood to the brain may become blocked and cause what is commonly referred to as a stroke. As is well known, a stroke often results in lasting disability and can result in death. Further, portions of the aorta, which is a major artery within the body that conveys blood from the heart to organs throughout the body, may become diseased, particularly in the abdominal region. A diseased aorta can cause severe pain and may eventually form an aneurysm that ruptures and causes death. Still further, femoral and popliteal arteries may become blocked. Typically, blockages in the femoral and popliteal arteries form near the groin and legs and cause weakness in the legs. If these blockages in the femoral and popliteal arteries are not diagnosed and treated in a timely manner, amputation of one or both legs may be required. Still further, the renal arteries, which convey blood from the abdominal aorta to the kidneys, may become blocked, thereby causing hypertension, kidney failure and ultimately death.

One particularly problematic vascular condition occurs in patients that have chronic renal (i.e., kidney related) failure. As is well known, renal dialysis and vascular access to carry out the dialysis are critical aspects of managing chronic renal failure. In fact, without some form of dialysis, the more than 120,000 people in the United States with chronic renal failure would rapidly succumb to their disease.

Hemodialysis is the most commonly employed renal dialysis technique. To effectively carry out hemodialysis, large needles must be inserted into large blood vessels so that substantial quantities of blood can be processed by the dialysis equipment in a relatively short period of time. Additionally, because hemodialysis must typically be performed several times each week for months or possibly years, arterial-venous (AV) access shunts are needed to provide long-term vascular access. As is well known, an AV shunt interposes between an artery and a vein, usually located in the patient's forearm, to enable blood to flow directly between the artery and the vein. The AV shunt provides the large blood vessel that is needed to accommodate the relatively large dialysis needle and bypasses high resistance vessels such as arterioles and capillaries to facilitate the high blood flow rates needed to accomplish efficient hemodialysis. Practically speaking, an AV shunt may be created by surgically placing a graft, which is typically either made of an artificial material or is scavenged from a vessel in another location of the body such as, for example, the leg. Alternatively, the AV shunt may be a fistula, which is created using direct anastomosis of an artery and a vein.

While the above-described AV shunts initially function properly, these AV shunts typically become clogged (with blood clots, for example, which may be caused by hyperplasia) over time. Furthermore, although there are a variety of techniques which can be used to treat (i.e., eliminate or reduce) vascular blockages such as, for example, angioplasty, early diagnosis of the blockage is needed to minimize risk to the patient and to maximize the likelihood that treatment will successfully reduce the blockage to a safe level or eliminate the blockage completely.

Further, because of the limited number of areas on a patient's body which may be used for hemodialysis access, it is crucial that access sites are preserved as long as possible. AV grafts account for about 75% of dialysis access devices and over one-half of these AV grafts require angioplastic or other salvage intervention within the first year. With AV fistulas, on the other hand, about 30% are unusable due to a failure to mature. Additionally, of the AV fistulas that successfully mature, about 15% require radiologic or surgical revision within one year.

At present, physical examination is a commonly used technique for assessment of vascular patency. Physical examination techniques are particularly useful for detecting very low blood flow which, in the case of an AV shunt, is indicative of an impending shunt failure. As is well known, vascular flux pulse and thrill (i.e., a vascular murmur) and auscultation may be used to assess vascular patency. Generally speaking, a palpable murmur or thrill is indicative of a reasonable blood flow (e.g., greater than about 450 milliliters/minute), a sharp pulse indicates lower blood flows and an increased bruit (i.e., an abnormal sound) suggests a vascular stricture or stenosis. Longitudinal monitoring of blood flow is another well known technique for detecting significant vascular stenosis. However, longitudinal monitoring techniques are less desirable in practice because these techniques require standardization of tubing size, needle size and other hemodialysis equipment. Still further, duplex color Doppler ultrasound flow studies, dilution and magnetic resonance imaging are other well known techniques for assessing vascular patency. Unfortunately, these conventional techniques are relatively expensive, of limited availability and the results obtained with these conventional techniques depend heavily on the skill level of the observer.

SUMMARY OF THE INVENTION

Acoustic detection techniques and apparatus described herein enable the non-invasive assessment of vascular conditions within a human or animal body. Generally speaking, the acoustic detection techniques and apparatus described herein measure vibrations or sounds generated by blood flowing through shunts, arteries and/or veins and process these measured vibrations or sounds to diagnose the internal condition of the shunts, arteries and/or veins. In particular, the acoustic detection techniques and apparatus described herein may be used to assess vascular patency in, for example, an AV shunt that provides vascular access for dialysis procedures. Thus, the acoustic detection techniques and apparatus described herein may be used to determine if a critical AV shunt has failed or is near failure, thereby reducing the possibility that a dialysis patient will be subjected to a life threatening condition.

More generally, the acoustic detection techniques and apparatus described herein may be used in a variety of applications in which non-invasive assessment of vascular conditions is desired. For example, the acoustic detection techniques and apparatus may be used to locate a vascular blockage and to assess the degree of the blockage. In particular, the acoustic detection techniques and apparatus may be used to detect blockages in carotid arteries to help prevent strokes, may be used to detect stenosis within renal arteries, may be used for early detection of abdominal aortic aneurysms, may be used to facilitate salvage of a femoral-popliteal bypass graft, etc.

DETAILED DESCRIPTION OF THE PREFERRED EMBODIMENTS

Generally speaking, the apparatus and techniques described herein may be used to acoustically detect vascular conditions. More specifically, the acoustic detection techniques and apparatus described herein may be used to detect vibrations or sounds imparted by blood flow to shunt, artery and/or vein walls. Sensors placed near or on the skin surface may then be used to convert these flow-induced vascular vibrations or sounds into electrical signals that are subsequently processed to determine the conditions within the underlying vascular system. The electrical signals may be processed to generate temporal and/or spectral information that may be indicative of a condition such as, for example, the patency, within a vascular structure. For instance, the temporal and/or spectral information generated using the techniques and apparatus described herein may be used to assess the condition of an AV shunt that is used for renal dialysis by comparing the generated temporal and/or spectral information to reference temporal and/or spectral information which is associated with a predetermined normal or acceptable vascular condition. Thus, the acoustic detection techniques and apparatus described herein may be used to non-invasively determine if vascular compromise, or any other vascular abnormality, is present.

While the acoustic detection techniques and apparatus are specifically described herein in connection with the assessment of vascular patency within an AV shunt, the techniques and apparatus are more generally applicable to a wide variety of applications and may be used to detect abnormalities such as, for example, occlusions or stenoses within veins or arteries that carry blood to any organ, or any other portion, of a body. For example, the acoustic detection techniques and apparatus described herein may be used to detect compromise (e.g., an occlusion or stenosis) within one or more of the carotid arteries, thereby enabling medical professionals to take measures to prevent a stroke.

Figure 1:
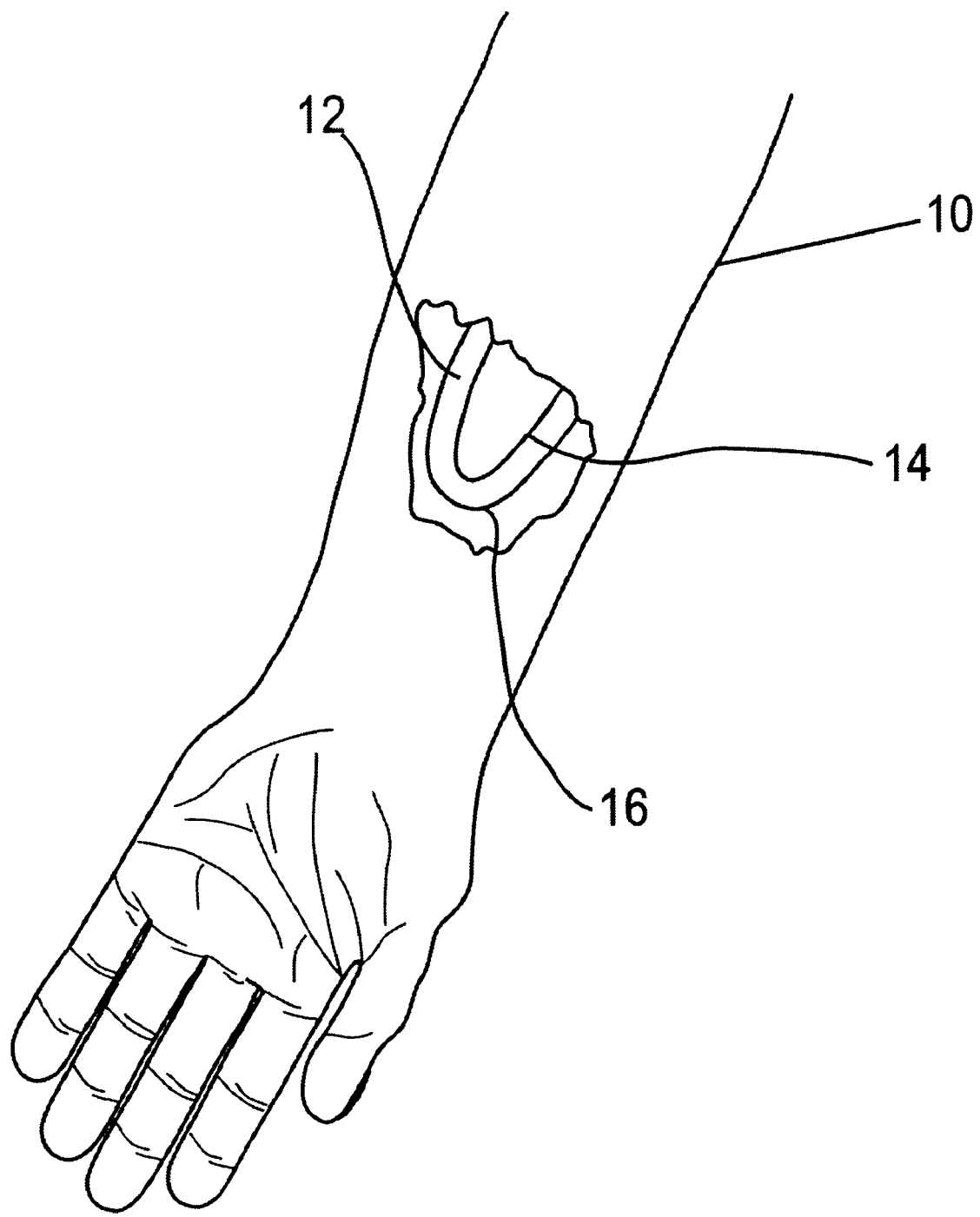
FIG. 1 is an exemplary diagrammatic cut-away view of a human forearm that illustrates the vascular anatomy for a typical renal dialysis arterio-venous (AV) shunt.

FIG. 1 is an exemplary diagrammatic cut-away view of a human forearm 10 that illustrates the vascular anatomy for a typical renal dialysis AV shunt. As shown in FIG. 1 by way of example only, an artery 12 and a vein 14 are connected to one another via a shunt 16 which, as described above, may be implemented using a graft or a fistula.

Figure 2:
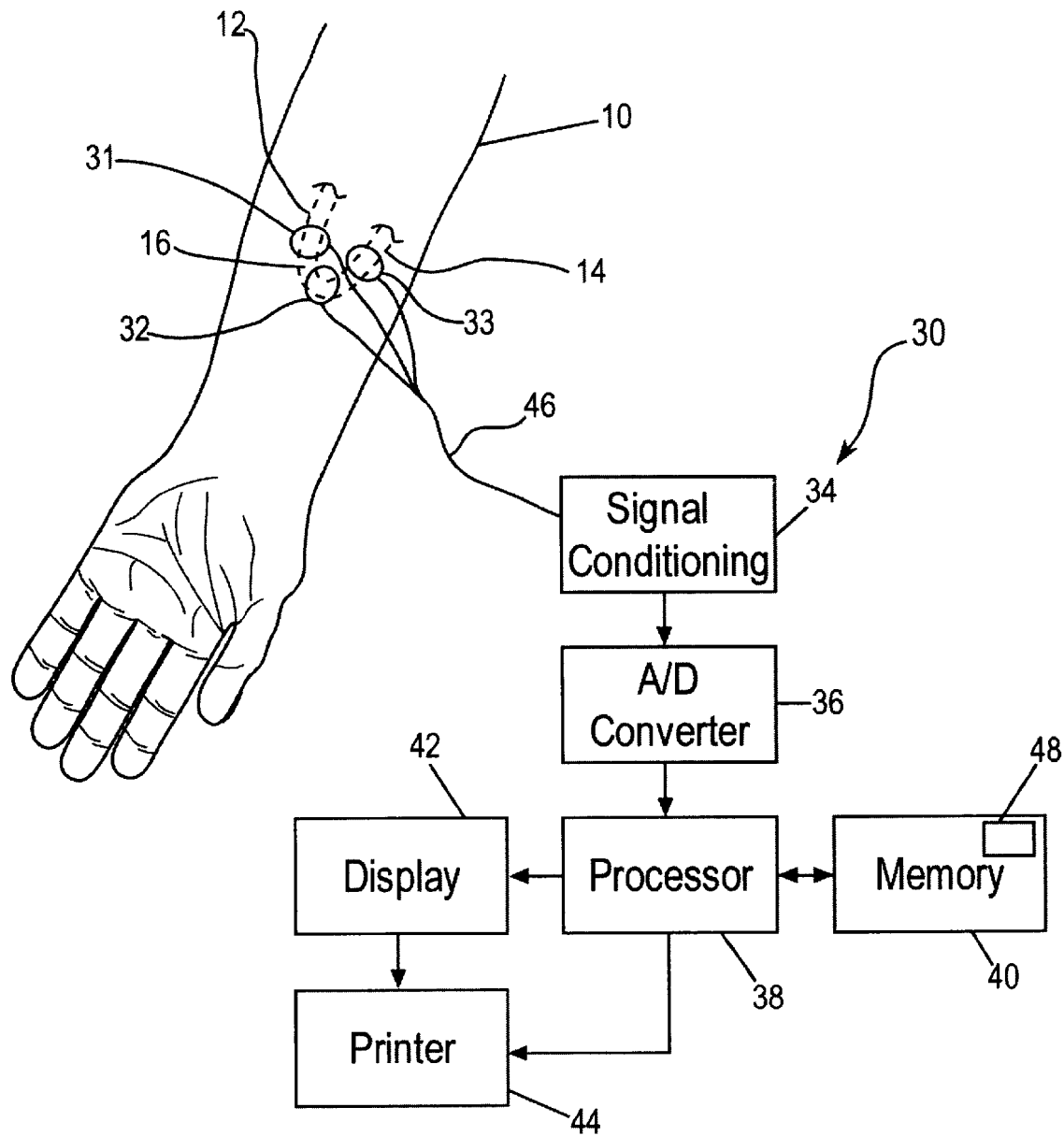
FIG. 2 is an exemplary schematic block diagram of an apparatus that may be used to assess the conditions within the shunt shown in FIG. 1.

FIG. 2 is an exemplary schematic block diagram of a system 30 that may be used to assess the conditions within the shunt 16 shown in FIG. 1. As shown in FIG. 2, the system 30 includes sensors 31–33, a signal conditioning block 34, an analog-to-digital (A/D) converter 36, a processor 38, a memory 40, a display 42 and a printer 44.

The sensors 31–33 may be contact or non-contact transducers that detect vibrations or sounds at or near the skin surface and convert these vibrations or sounds into electrical signals. By way of example only, the sensors 31–33 may be electronic stethoscopes, accelerometers, contact microphones, non-contact vibration sensors such as capacitive or optical sensors, or any other suitable type of sensors. In some applications, an electret condenser air-coupled electronic stethoscope design may be selected for its sensitivity over a wide bandwidth, low cost, durability and ease of use. In any event, the sensors 31–33 are preferably, but not necessarily, selected to have an impedance that matches the impedance of the skin surface to provide optimal coupling to the skin surface. Still further, due to background noise and the relatively low amplitude of the vibrations or sounds which are generated at or near the skin surface by vascular blood flow, the sensors 31–33 are also preferably, but not necessarily, selected to provide a high signal-to-noise ratio, high sensitivity and good ambient noise shrouding capability. While three sensors are shown in FIG. 2, additional or fewer sensors may be used to detect vascular vibrations or sounds at multiple locations on the patient's forearm 10, or any other locations on the patient's body that are of interest. For example, a single sensor may be strategically located on the patient's body and/or may be moved sequentially to different key locations on the patient's body to detect vascular vibrations or sounds.

The sensors 31–33 send low level (i.e., low power) electrical signals via wires 46, or any other suitable media such as wireless radio frequency, infrared, etc., to the signal conditioning block 34. The signal conditioning block 34 may include amplifiers, filters, transient protection and other circuitry that amplifies the signals sent by the sensors 31–33, attenuates noise signals, and reduces the effects of aliasing. In particular, the signal conditioning block 34 may include a low-pass filter having a cutoff frequency of about 2000 Hertz (Hz). Alternatively or additionally, a high-pass filter may be incorporated within the signal conditioning block 34. This high-pass filter may, for example, have a cut-off frequency of about 75 Hz so that undesirable noise, such as muscle noise or other low frequency noise, is substantially attenuated or eliminated before the signals sent by the sensors 31–33 are processed further.

The A/D converter 36 receives the signal conditioned analog output signals from the signal conditioning block 34 and converts the received analog signal values into digital vibration information, which can be processed by the processor 38, as described in greater detail below. The processor 38 may be integral to a personal computer, may be integral to a microcontroller integrated circuit chip, may be implemented using a custom integrated circuit chip, or may be implemented using any other electronic device suitable for carrying out the methods described herein.

The memory 40 is communicatively coupled to the processor 38 and may include software 48 that, when executed by the processor 38, causes the processor 38 to carry out the methods described herein. It should be recognized that the processor 38 and the memory 40 may be integral to a personal computer or, alternatively, may be implemented using one or more custom, semi-custom or commonly available integrated circuits. Further, it should be recognized that the software 48 may include one or more software routines that are implemented using any of a variety of programming techniques and languages without departing from the scope and the spirit of the invention.

The display 42 may be any conventional video monitor or any other suitable display that communicates with the processor 38 and which can display graphic and/or textual information relating to the vascular sounds and vibrations detected by one or more of the sensors 31–33. Thus, the information generated on the display 42 may facilitate medical personnel in making a diagnosis of the vascular conditions within a patient's body. For example, the display 42 may graphically represent the temporal and/or spectral characteristics of the vascular sounds or vibrations detected at a particular location of the patient's body, which may be associated, for example, with a critical vascular structure such as an artery that supplies blood to a critical organ or a shunt, which is typically susceptible to stenosis and a variety of other pathologies. The displayed temporal and/or spectral characteristics may then be used to determine if an abnormal vascular condition exists by, for example, comparing the acquired temporal and/or spectral characteristics to reference temporal and/or spectral characteristics associated with a normal or acceptable condition. In addition, the acquired temporal and/or spectral characteristics may further be used to determine the precise location, type and severity of any abnormal condition present.

The printer 44 may be used to generate hard copies of textual and/or graphical information, including the information which is displayed on the display 42. For example, numerical and graphical temporal and/or spectral information may be printed to facilitate off-line analysis of test results by medical personnel and/or to facilitate the generation of permanent test results documentation for records, reports, etc.

Before discussing the operation of the system 30 shown in FIG. 2 in more detail, a general discussion of the acoustic characteristics of vascular blood flow is provided below. In general, the partial occlusion of blood flow causes the turbulence characteristics of the blood flow to change. These turbulence characteristics, in turn, are manifested as vibrations or sounds that can be detected at the skin surface. As will be described in greater detail below, an occluded or stenotic condition may cause the spectral energy of these turbulence induced vibrations or sounds to shift toward higher frequencies slightly downstream of the occlusion or stenosis. Additionally, as will also be discussed in greater detail below, relative acoustic spectral changes over an affected anastomotic region may be indicative of an occlusion.

As is well known, fluid flowing through a conduit produces turbulence which, in turn, may produce sounds in the audible frequency range. The characteristics of these audible turbulence sounds are determined by many variables, including conduit course and geometry, flow volume and velocity, conduit dimensions, conduit wall elasticity, etc.

More specifically, as fluid approaches a narrowed cross-section within the conduit the fluid velocity increases and the fluid flow characteristics in the narrowed region depend on the conduit geometry and flow properties associated with the Reynolds number. For example, when there is only a slight decrease in conduit diameter and/or when the Reynolds number is low (e.g., due to a low fluid velocity), the fluid attaches to the conduit wall and typically only small vibrations are imparted to the conduit wall.

On the other hand, where there is a large decrease in conduit diameter and/or a high Reynolds number (e.g., due to high flow velocities), the fluid typically detaches from the conduit wall. Slightly downstream of the minimum cross-sectional area (which is the same as the minimum diameter point if the cross-section is substantially circular), at a point called the vena contracta, the fluid attains a maximum velocity and minimum pressure. Then, as the flow area increases, the flow reattaches to the conduit wall and the average flow velocity decreases. In the case of vascular blood flow, the detached flow region may extend significantly downstream. For example, for an 85% stenosis and a Reynolds number of 200–2000, the blood flow may reattach to the vessel wall two to four vessel diameters downstream from the region of minimum cross-section (i.e., the stenosis).

When the Reynolds number is more than 325, the shear layer that forms in the detached flow region becomes highly unstable and causes strong velocity fluctuations or turbulence. This turbulence in the shear layer downstream of the constriction (e.g., a stenosis) causes relatively large conduit wall pressure oscillations, which may be coupled to neighboring structures. The amplitude of these wall pressure variations is a measure of turbulence intensity and is known to increase as the Reynolds number increases.

Figure 3:
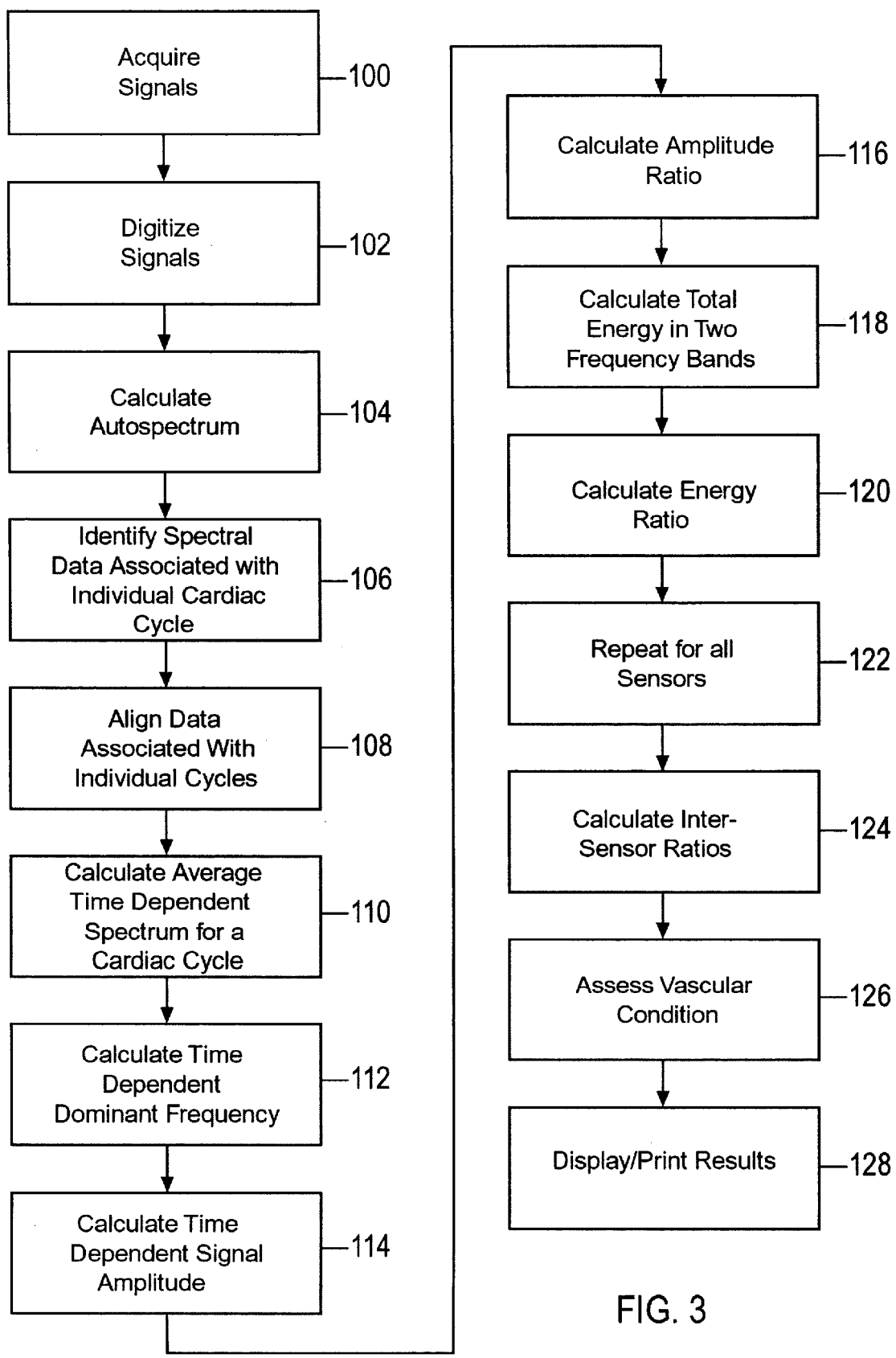
FIG. 3 is an exemplary flow diagram that represents one method by which the apparatus shown in FIG. 2 may process acoustic signals to assess the conditions within the shunt shown in FIG. 1.

FIG. 3 is an exemplary flow diagram that represents one method by which the apparatus shown in FIG. 2 may process acoustic signals to assess the conditions within the shunt 16 shown in FIG. 1. Block 100 acquires analog electrical signals from one or more of the sensors 31–33 (FIG. 2). Block 100 may use the signal conditioning block 34 (FIG. 2) to filter noise, amplify the signals, etc. as discussed above before the signals are processed by block 102. Further, block 100 may acquire signals from one or more of the sensors 31–33 for a period of time sufficient to capture vascular sounds or vibrations that are generated during one or more cardiac cycles. For example, block 100 may acquire signals from one or more of the sensors 31–33 for a period of time equal to the time required to complete ten cardiac cycles. Of course, block 100 may acquire sounds or vibrations for a period of time that corresponds to more or fewer cardiac cycles without departing from the scope of the invention.

The sensors 31–33 may be arranged in any desired manner to facilitate the acquisition of vibrations and sounds associated with vascular blood flow turbulence and to facilitate the detection of vascular pathologies such as, for example, stenoses, occlusions, etc. In particular, in the case of the shunt 16, one of the sensors 31–33 (e.g., the sensor 32) may be located directly over the central portion of the shunt 16 (the location of which is typically precisely known because it is surgically placed) and the sensors 31 and 33 may be located upstream and downstream, respectively. Alternatively, the sensors 31 and 32 may be eliminated and the sensor 33 may be used to acquire signals representative of the acoustic characteristics of the shunt 16 in a region adjacent to a suspected stenosis or occlusion. Additionally, the sensor 33 may be moved to locations other than that specifically depicted in FIG. 2 without departing from the scope and the spirit of the invention.

Block 102 converts the analog signals acquired by block 100 into digital data or information using, for example, the A/D converter 36 shown in FIG. 2. Typically, but not necessarily, the analog data is digitized at a sampling rate of 8192 Hz. However, other sampling rates may be used to achieve any desired frequency resolution.

Block 104 calculates the time dependent autospectrum (i.e., the time dependent spectral characteristics) of the digitized data provided by block 102. As is well known, the autospectrum may be graphically represented using a three-dimensional plot in which the x and y axes correspond to time and frequency and the z axis corresponds to spectral power. See, for example, FIGS. 7 and 8. Typically, but not necessarily, the autospectrum is calculated by performing fast Fourier transforms (FFTs) on overlapping segments of the digitized data. For example, if a 1024 point FFT is desired, the data segments may be defined as 125 milliseconds (ms) in duration with a 50% overlap. However, different data segment lengths and overlap percentages may be used instead to achieve any desired time and frequency resolution. Additionally, other data analysis techniques or algorithms such as autoregressive modeling or wavelets may be used instead of or in addition to FFTs to transform the digitized analog data into frequency domain or spectral information.

Block 106 identifies the spectral data associated with each of the individual cardiac cycles using any suitable data analysis technique. For example, autocorrelation of the acquired signals, autocorrelation of the acquired signal envelope and/or autocorrelation of the time dependent spectrum may be used to identify those portions of the spectral data produced by block 104 that are associated with each of the cardiac cycles for which block 100 has acquired signals. Block 108 then temporally aligns the portions or groups of spectral data associated with the individual cardiac cycles. This temporal alignment may be performed, for example, by aligning spectral peaks or by searching for the best time shift by calculating the autocorrelation of the time dependent spectrum at different frequencies. Of course, where block 100 only acquires data for a single cardiac cycle, blocks 106 and 108 do not necessarily have to be performed.

Block 110 uses the temporally aligned groups of spectral data generated by block 108 to calculate an average time dependent spectrum for the cardiac cycles. Block 110 may, for example, average (i.e., ensemble average) the temporally aligned time dependent spectra for each of the cardiac cycles. However, any other averaging technique that produces the time dependent spectral characteristics for a typical cardiac cycle may be used instead. Block 112 then uses the average time dependent spectrum for a typical cardiac cycle calculated by block 110 to determine the time dependent dominant frequency, which is the frequency having the largest spectral energy at each instant of time. See, for example, FIGS. 9 and 11.

Block 114 uses the time dependent spectrum for an average cardiac cycle to calculate the time dependent signal amplitude of the average cardiac cycle by summing the energies of all frequency data points at each instant of time. Alternatively, block 114 may calculate the time dependent signal amplitude of the average cardiac cycle by determining the amplitude of the Hilbert transform of the blood flow acoustic signals. Block 116 then determines the amplitudes associated with the time dependent signal amplitude of the average cardiac cycle, which is generated by block 114, at two different parts of the average cardiac cycle. For example, the points within the average cardiac cycle that correspond to the minimum and maximum amplitudes may be selected. After block 116 has determined the amplitudes, block 116 calculates the ratio of the amplitudes.

Block 118 uses the average time dependent spectrum calculated in block 110 to calculate the total energy in two or more predetermined frequency bands. By way of example only, the frequency bands may be 50–175 Hz and 200–400 Hz. However, other frequency bands may be used instead without departing from the scope of the invention. Further, the total energy within the predetermined frequency bands may be calculated over all parts of the cardiac cycle (i.e., using the total spectral power for a single cardiac cycle) by summing the spectral power for each frequency of the time dependent spectrum over all time intervals.

Alternatively, the total energy within the predetermined frequency bands may be calculated at different parts of the cardiac cycle. In other words, the total energy within one of the predetermined frequency bands may be calculated at one time within the cardiac cycle and the total energy within another one of the predetermined frequency bands may be calculated at a different time within the cardiac cycle (using the time dependent spectrum calculated by block 110). Block 120 then uses the total energy values calculated by block 118 to calculate energy ratios. For example, the total energy associated with a high frequency band (e.g., 200 Hz to 400 Hz) may be divided by the total energy associated with a low frequency band (e.g., 50 Hz to 175 Hz).

Block 122 may then repeat the activities of blocks 100 through 120 for all of the sensors (e.g., the sensors 31–33) that are currently being used to detect vascular sounds and vibrations and block 124 may use data associated with two or more of the sensors 31–33 to calculate inter-sensor amplitude ratios and/or inter-sensor energy ratios. Block 126 may then use the time dependent dominant frequency information, the amplitude ratios and/or the energy ratios for one or more of the sensors 31–33 to assess the patient's vascular condition. Alternatively or additionally, the inter-sensor ratios may be used to assess the patient's vascular condition.

While the system 30 shown in FIG. 2 is described by way of example as being adapted to process the acoustic signals acquired by the sensors 31–33 using digital signal processing techniques, analog signal processing techniques may be used instead to process vibration or sound information to achieve the same or similar results. For example, an analog filter bank may be used to separate the energy associated with different energy bands and one or more comparators may be used to make relative comparison between the energy values of the different bands.

As will be discussed in greater detail below in connection with FIGS. 5–12, the acoustic characteristics associated with different vascular conditions may vary significantly from one condition to another. Thus, the acoustic characteristics associated with each known vascular condition may be determined in advance and parameter values such as, for example, values for the time dependent dominant frequency, the amplitude ratio and/or the energy ratios may be developed for each vascular pathology. In this manner, block 126 may assess a patient's vascular condition by comparing the calculated dominant frequency, amplitude ratio and/or energy ratio values to one or more sets of predetermined parameter values, each of which contains values that are indicative of a particular vascular condition or pathology. Further, block 126 may use neural network techniques, which are well known, to produce a resultant value based on one or more of the calculated parameters.

In addition, for some vascular conditions, patient to patient variability may be substantial, which significantly reduces or eliminates the discriminatory power that a predetermined set of parameter values affords the assessment of vascular condition performed by block 126. For assessment of vascular conditions in which between patient variability is relatively high, a set of baseline parameter values may be developed for each patient and relative comparisons of calculated parameter values to these baseline values may be made to more precisely assess the vascular conditions within that particular patient.

Figure 4:
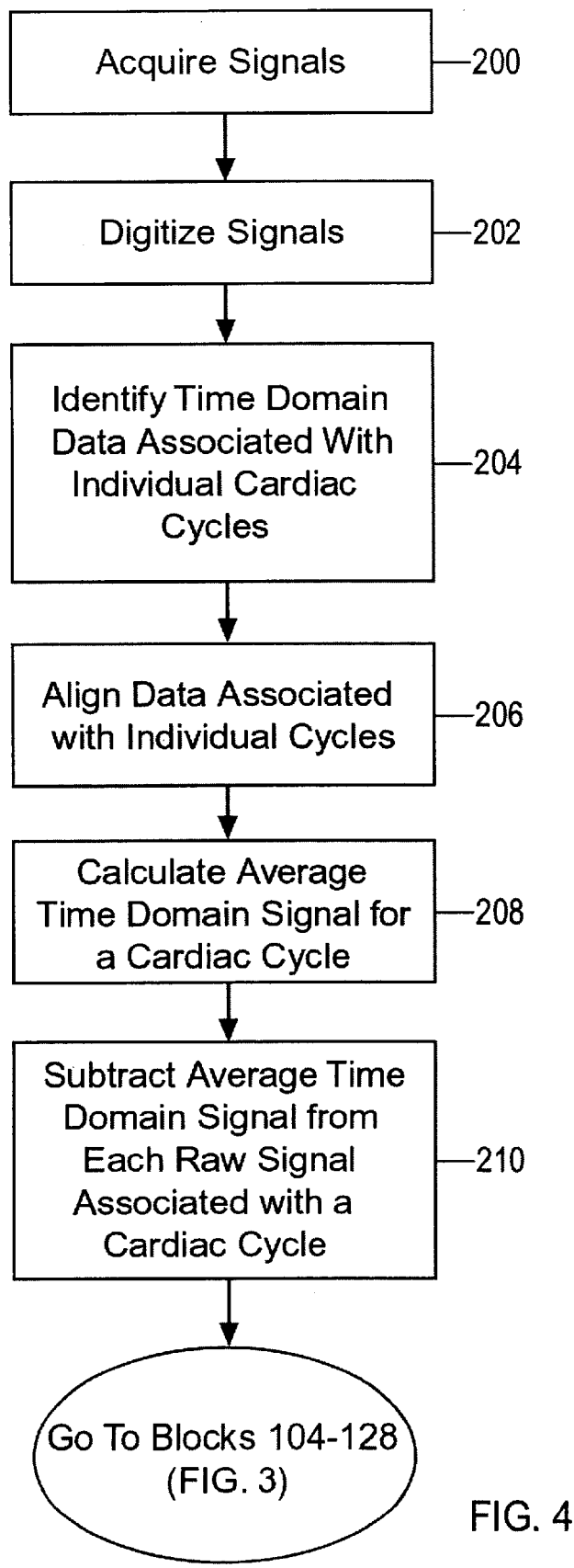
FIG. 4 is an exemplary flow diagram that represents another method by which the apparatus shown in FIG. 2 may process acoustic signals to assess the conditions within the shunt shown in FIG. 1.

FIG. 4 is an exemplary flow diagram that illustrates another method by which the apparatus shown in FIG. 2 may process acoustic signals to assess the conditions within the shunt 16 shown in FIG. 1. Blocks 200 and 202 acquire and digitize signals in manners identical to that of blocks 100 and 102, the operations of which are described above in connection with FIG. 3. Block 204 then identifies the groups of time domain data that are associated with each of the individual cardiac cycles and block 206 temporally aligns the groups of time domain data identified by block 204. Block 206 may use any suitable technique such as, for example, autocorrelation of the time domain signal or signal amplitude calculated as in block 114 above, to perform the temporal alignment.

Block 208 then averages the temporally aligned groups of time domain data generated by block 206 to calculate the time domain signal for an average cardiac cycle. Block 210 then subtracts this average time domain signal from each of the groups of time domain information (i.e., the individual cardiac cycles) identified by block 204. In this manner, block 210 produces difference signals which are representative of the non-repeatable or non-cyclical portions of each cardiac cycle acquired by block 200. The characteristics of these difference signals (i.e., the non-repeatable acoustic information) may then be processed by blocks 104–128 shown in FIG. 3, thereby enabling an assessment of a patient's vascular condition based on non-repeatable signal characteristics.

Figure 6:
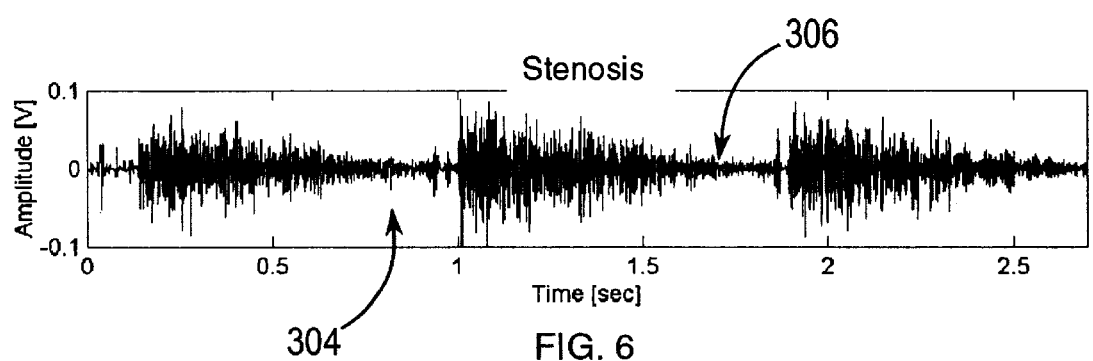
FIG. 6 is an exemplary graphical representation of an electrical signal obtained by measuring the sounds generated within a vascular shunt having a stenosis.
Figure 5:
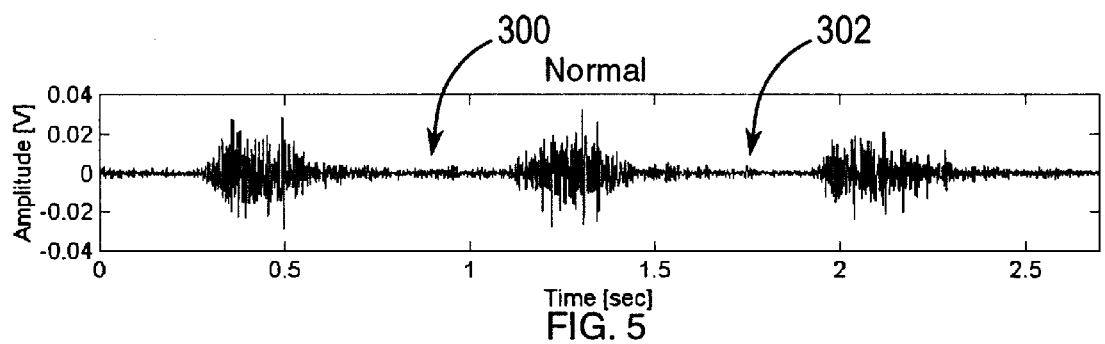
FIG. 5 is an exemplary graphical representation of an electrical signal obtained by measuring the sounds generated within a vascular shunt having normal patency.

FIG. 5 is an exemplary graphical representation of an electrical signal obtained by measuring the sounds generated at the skin surface adjacent to a vascular shunt having normal or acceptable patency. FIG. 6, on the other hand, is an exemplary graphical representation of an electrical signal obtained by measuring the sounds generated at the skin surface adjacent to a vascular shunt having a stenosis. The electrical signals shown in FIGS. 5 and 6 are more than 2.5 seconds in duration and, in this case, include vascular sounds generated during three cardiac cycles. The electrical signals may be acquired, for example, using the methods shown in FIGS. 3 and 4 in conjunction with the apparatus 30 shown in FIG. 2. More specifically, blocks 100 and/or 200 may acquire the signals using one or more of the sensors 31–33 and the signal conditioning block 34. Of course, the electrical signals may be acquired over a longer or a shorter time period and, thus, may include more or fewer cardiac cycles, if desired.

A comparison of the signals shown in FIGS. 5 and 6 reveals that the peak-to-peak amplitudes of the signal generated when a stenosis exists within the vascular structure being monitored is, generally speaking, much greater than the peak-to-peak amplitudes of the signal generated under normal conditions (i.e., when the stenosis is relieved, eliminated or absent). In particular, FIG. 6 shows, by way of example only, a peak-to-peak amplitude of about 200 millivolts (mV), whereas FIG. 5 shows a peak-to-peak amplitude of less than about 75 mV. Further, it can be seen from FIGS. 5 and 6 that the noise level present in the regions between cardiac cycles, such as the regions 300 and 302 shown in FIG. 5, is relatively low compared to the corresponding regions 304 and 306 shown in FIG. 6.

Figure 8:
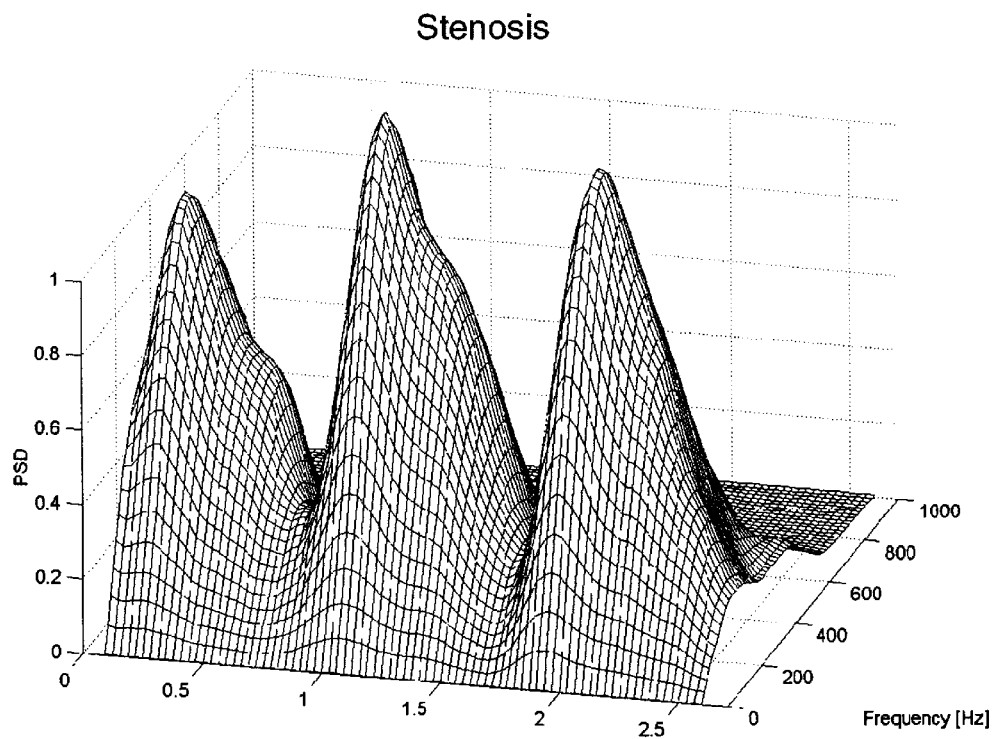
FIG. 8 is an exemplary graphical representation of the time dependent spectral characteristics of the electrical signal shown in FIG. 6.
Figure 7:
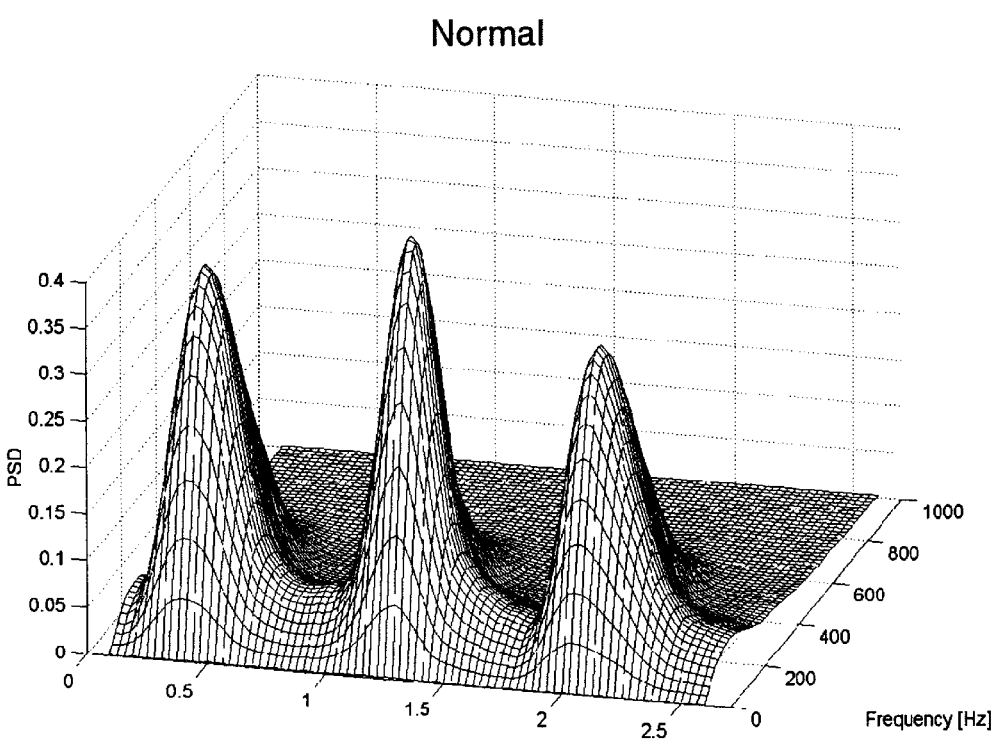
FIG. 7 is an exemplary graphical representation of the time dependent spectral characteristics of the electrical signal shown in FIG. 5.

FIG. 7 is an exemplary graphical representation of the time dependent spectral characteristics of the electrical signal shown in FIG. 5 and FIG. 8 is an exemplary graphical representation of the time dependent spectral characteristics of the electrical signal shown in FIG. 6. Thus, the spectral characteristics shown in FIG. 7 are associated with a normal vascular condition, whereas the spectral characteristics shown in FIG. 8 are associated with a stenotic vascular condition. As can be clearly seen from FIGS. 7 and 8, the spectral power associated with a wide range of frequencies appears to increase substantially when a stenotic vascular condition is present. As noted above, this increased spectral power may be directly due to the increased turbulence that a stenosis produces slightly downstream of or adjacent to the stenotic region.

Figure 12:
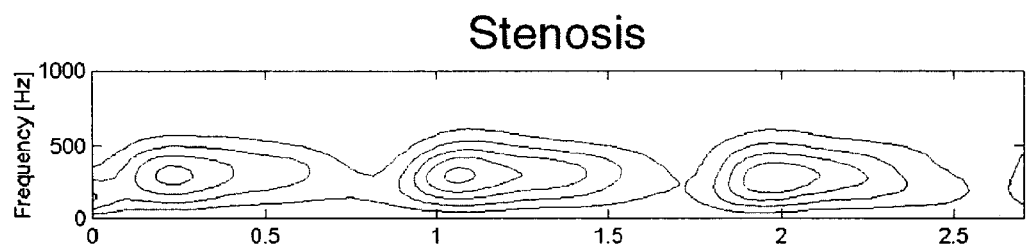
FIG. 12 is an exemplary contour plot of the time dependent spectral characteristics shown in FIG. 8.
Figure 11:
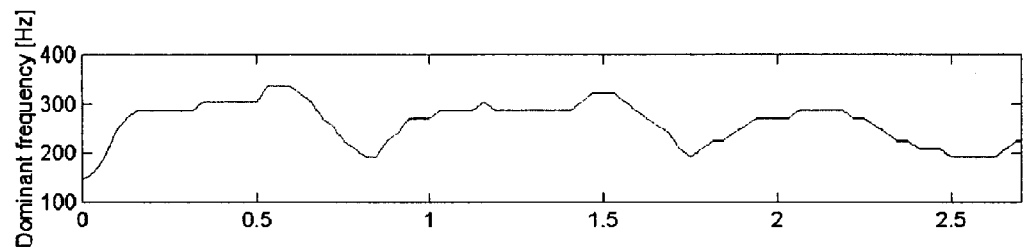
FIG. 11 is an exemplary graphical representation of the time dependent dominant frequency of the electrical signal shown in FIG. 6.
Figure 10:
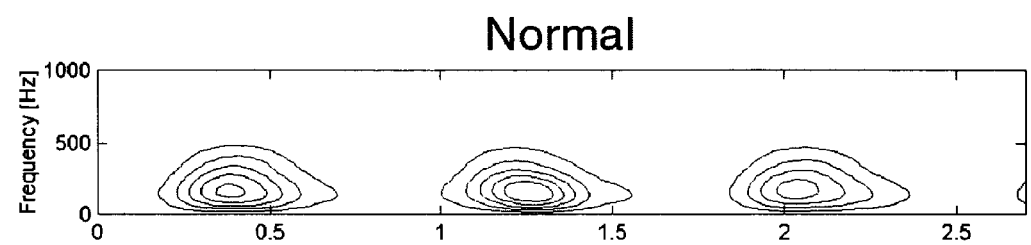
FIG. 10 is an exemplary contour plot of the time dependent spectral characteristics shown in FIG. 7.
Figure 9:
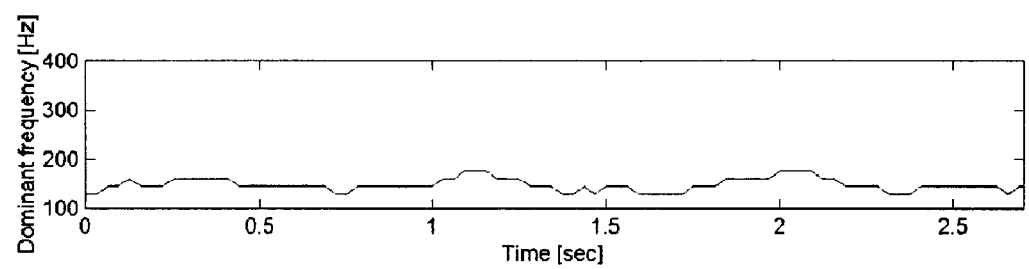
FIG. 9 is an exemplary graphical representation of the time dependent dominant frequency of the electrical signal shown in FIG. 5.

FIG. 9 is an exemplary graphical representation of the time dependent dominant frequency of the electrical signal shown in FIG. 5 and FIG. 10 is an exemplary contour plot of the time dependent spectral characteristics shown in FIG. 7. Similarly, FIG. 11 is an exemplary graphical representation of the time dependent dominant frequency of the electrical signal shown in FIG. 6 and FIG. 12 is an exemplary contour plot of the spectral characteristics shown in FIG. 8. As clearly shown by FIGS. 9–12, the temporal and/or spectral characteristics associated with a normal vascular condition are significantly different from the temporal and/or spectral characteristics associated with a stenotic vascular condition.

In any event, the significant differences in the temporal and/or spectral characteristics, which are depicted by way of example in FIGS. 5–12, may be used in conjunction with the methods described herein to detect the location and/or type and degree of a vascular abnormality.

In one test on a 65 year old female suspected to have AV graft stenosis, the methods and apparatus described herein were used to measure acoustic characteristics both before and after angioplasty of an affected region associated with the graft. A 90% stenotic region was found and was verified to improve by 50% post angioplasty.

After digitization at 8192 Hz, the power spectral density was calculated using a FFT with Hanning windowing to provide a resolution of about 16 Hz. The mean spectral densities were then calculated for pre and post angioplasty states by averaging the data from each 125 ms acquisition segment. The dominant frequency was then found by determining the frequency having the highest power level within the mean spectral density function. In a pre-angioplasty state the dominant frequency was found to be 270+/−74 Hz and in the post angioplasty state the dominant frequency was found to be 125+/−31 Hz. A Z-test was used to determine the statistical significance of the results. In this case, the Z-test resulted in a p value of 0.03, which indicates a high probability that a shift of spectral energy had in fact occurred.

If implemented in software, the functions and routines discussed herein may be stored in any computer readable memory such as on a magnetic, an optical, or other storage medium, in a RAM or ROM of a computer, controller, field device, etc. Likewise, this software may be modulated on a carrier and delivered to a user or a device via any known or desired delivery method including, for example, over a communication channel such as a telephone line, the Internet, etc.

While the invention has been described with reference to specific examples, which are intended to be illustrative only and not to be limiting of the invention, it will be apparent to those of ordinary skill in the art that changes, additions or deletions may be made to the disclosed embodiments without departing from the spirit and the scope of the invention.

What is claimed is:

1. A method of detecting a vascular condition, the method comprising:
   receiving sound information associated with blood flowing through a vascular structure;
   converting the sound information into temporal data associated with a plurality of cardiac cycles;
   averaging the temporal data to form a set of average data; and
   detecting the vascular condition based on a difference between the temporal data and the set of average data.

2. The method of claim 1, wherein receiving the sound information includes receiving a signal from at least one vibration sensor.

3. The method of claim 1, wherein receiving the sound information includes receiving sound emitted in response to the blood flowing through one of a shunt, a vein and an artery.

4. The method of claim 1, further comprising generating spectral information associated with the difference between the temporal data and the set of average data.

5. The method of claim 4, wherein detecting the vascular condition includes detecting the vascular condition based on a spectral parameter associated with the spectral information.

6. The method of claim 5, wherein detecting the vascular condition based on the spectral parameter includes comparing the spectral parameter to a reference value.

7. The method of claim 6, wherein comparing the spectral parameter to the reference value includes comparing the spectral parameter to a value indicative of an abnormal vascular condition.

8. The method of claim 7, wherein comparing the spectral parameter to the value indicative of the abnormal vascular condition includes comparing the spectral parameter to a value associated with at least one of a vascular patency, a vascular occlusion and a vascular stenosis.

9. The method of claim 1, wherein converting the sound information into the temporal data associated with the plurality of cardiac cycles includes aligning groups of data, each of which is associated with one of the plurality of cardiac cycles.

10. The method of claim 1, wherein averaging the temporal data to form the set of average data includes identifying groups of temporal data, each of which is associated with one of the plurality of cardiac cycles, and averaging the groups of temporal data to generate data representative of an average cardiac cycle.

11. A method of detecting a vascular condition, the method comprising:
    receiving vibrations emitted in response to blood flowing through a vascular structure;
    converting the received vibrations into vibration information;
    generating spectral information from the vibration information;
    calculating a spectral parameter based on the spectral information, wherein calculating the spectral parameter based on the spectral information includes calculating a time dependent amplitude signal and calculating an amplitude ratio based on the time dependent amplitude signal; and
    detecting the vascular condition based on the spectral parameter.

12. The method of claim 11, further comprising calculating the spectral parameter based on a plurality of energy values associated with a respective plurality of frequency bands within the spectral information and calculating an energy ratio based on the plurality of energy values.

13. A method of detecting a vascular condition, the method comprising:
    receiving vibrations emitted in response to blood flowing through a vascular structure;
    converting the received vibrations into vibration information;
    generating spectral information from the vibration information, wherein generating spectral information from the vibration information includes identifying groups of temporal data, each of which is associated with one of a plurality of cardiac cycles, and averaging the groups of temporal data to generate an average time domain signal representative of an average cardiac cycle, and wherein generating spectral information from the vibration information further includes subtracting the average time domain signal from each of the groups of temporal data;
    calculating a spectral parameter based on the spectral information; and
    detecting the vascular condition based on the spectral parameter.

14. A system for detecting a vascular condition body, the system comprising:
    a memory; and
    a processor communicatively coupled to the memory, wherein the processor is programmed to receive sound information, wherein the processor is programmed to convert the sound information into temporal data associated with a plurality of cardiac cycles, wherein the processor is programmed to average the temporal data to form a set of average data, and wherein the processor is programmed to detect the vascular condition based on a difference between the temporal data and the set of average data.

15. The system of claim 14, further comprising at least one vibration sensor operatively coupled to the processor and configured to detect the sound information.

16. The system of claim 15, wherein the vibration sensor is adapted to detect vibrations associated with blood flowing through a vascular structure.

17. The system of claim 16, wherein the vascular structure is one of a shunt, an artery and a vein.

18. The system of claim 14, wherein the processor is further programmed to generate spectral information associated with the difference between the temporal data and the set of average data.

19. The system of claim 18, wherein the processor is further programmed to detect the vascular condition based on a spectral parameter associated with the spectral information.

20. The system of claim 19, wherein the processor is further programmed to compare the spectral parameter to a reference value.

21. The system of claim 19, wherein the processor is further programmed to compare the spectral parameter to a value indicative of an abnormal vascular condition.

22. The system of claim 21, wherein the the abnormal vascular condition is associated with at least one of a vascular patency, a vascular occlusion and a vascular stenosis.

23. The system of claim 14, wherein the processor is further programmed to convert the sound information into the temporal data by aligning groups of data, each of which is associated with one of the plurality of cardiac cycles.

24. The system of claim 14, wherein the processor is further programmed to average the temporal data to form the set of average data by identifying groups of temporal data, each of which is associated with one of the plurality of cardiac cycles, and averaging the groups of temporal data to generate an average time domain signal representative of an average cardiac cycle.

25. A system for detecting a vascular condition, the system comprising:
a memory; and
a processor communicatively coupled to the memory, wherein the processor is programmed to receive vibration information, wherein the processor is programmed to generate spectral information from the vibration information and to calculate a spectral parameter based on the spectral information, and wherein the processor is programmed to detect the vascular condition based on the spectral parameter, and wherein the processor is further programmed to calculate a time dependent amplitude signal and to calculate an amplitude ratio based on the time dependent amplitude signal.

26. The system of claim 19, wherein the processor is further programmed to calculate the spectral parameter based on a plurality of energy values associated with a respective plurality of frequency bands within the spectral information and to calculate an energy ratio based on the plurality of energy values.

27. A system for detecting a vascular condition, the system comprising:
a memory; and
a processor communicatively coupled to the memory, wherein the processor is adapted to receive vibration information, wherein the processor is programmed to generate spectral information from the vibration information and to calculate a spectral parameter based on the spectral information, wherein the processor is programmed to detect the vascular condition based on the spectral parameter and to identify groups of temporal data, each of which is associated with one of a plurality of cardiac cycles, and to average the groups of temporal data to generate an average time domain signal representative of an average cardiac cycle, and wherein the processor is further programmed to subtract the average time domain signal from each of the groups of temporal data.

28. A machine readable medium having instructions stored thereon that, when executed, cause a machine to:
receive sound information associated with a vascular condition;
convert the sound information into temporal data associated with a plurality of cardiac cycles;
average the temporal data to form a set of average data; and
detect the vascular condition based on a difference between the temporal data and the set of average data.

29. The machine readable medium of claim 28, wherein the instructions, when executed, cause the machine to receive the sound information from a plurality of vibration sensors.

30. The machine readable medium of claim 28, wherein the instructions, when executed, cause the machine to generate spectral information associated with the difference between the temporal data and the set of average data.

31. The machine readable medium of claim 30, wherein the instructions, when executed, cause the machine to detect the vascular condition based on a spectral parameter associated with the spectral information.

32. The machine readable medium of claim 31, wherein the instructions, when executed, cause the machine to compare the spectral parameter to a reference value.

33. The machine readable medium of claim 32, wherein the reference value is associated with an abnormal vascular condition.

34. The machine readable medium of claim 33, wherein the the abnormal vascular condition includes at least one of a vascular patency, a vascular occlusion and a vascular stenosis.

35. The machine readable medium of claim 28, wherein the instructions, when executed, cause the machine to convert the sound information into the temporal data by aligning groups of data, each of which is associated with one of the plurality of cardiac cycle.

36. The machine readable medium of claim 28, wherein the instructions, when executed, cause the machine to identify groups of temporal data, each of which is associated with one of a plurality of the cardiac cycles, and to average the groups of temporal data to generate data representative of an average cardiac cycle.

37. A machine readable medium having instructions stored thereon that, when executed, cause a machine to:
receive vibration information associated with a vascular condition;
generate spectral information from the vibration information;
calculate a spectral parameter based on the spectral information by calculating a time dependent amplitude signal and calculating an amplitude ratio based on the time dependent amplitude signal; and
detect the vascular condition based on the spectral parameter.

38. The machine readable medium of claim 37, wherein the the instructions, when executed, cause the machine to calculate the spectral parameter by calculating a plurality of energy values associated with a respective plurality of frequency bands within the spectral information and calculating an energy ratio based on the plurality of energy values.

39. A machine readable medium having instructions stored thereon that, when executed, cause a machine to:

receive vibration information associated with a vascular condition;

generate spectral information from the vibration information;

calculate a spectral parameter based on the spectral information;

detect the vascular condition based on the spectral parameter; and identify groups of temporal data, each of which is associated with one of a plurality of cardiac cycles, and to average the groups of temporal data to generate an average time domain signal representative of an average cardiac cycle and to subtract the average time domain signal from each of the groups of temporal data.

* * * * *